United States Patent [19]

Harris

[11] Patent Number: 5,679,715

[45] Date of Patent: Oct. 21, 1997

[54] METHOD FOR TREATING MULTIPLE SCLEROSIS

[76] Inventor: Richard Y. Harris, 381 Rampart Range Rd., Woodland Park, Colo. 80863

[21] Appl. No.: 486,299

[22] Filed: Jun. 7, 1995

[51] Int. Cl.$^6$ .......................... A01N 33/02; A61K 31/135
[52] U.S. Cl. .............................................. 514/656; 558/390
[58] Field of Search .................................. 514/579, 656; 558/390

[56] References Cited

U.S. PATENT DOCUMENTS

| | | | |
|---|---|---|---|
| 5,453,428 | 9/1995 | Kaminski | 514/279 |
| 5,519,061 | 5/1996 | Youdin et al. | 514/647 |

OTHER PUBLICATIONS

Connelly, "Interferon Beta for Multiple Sclerosis", Annals of Pharmacotherapy, May 1994 28(5) 610–5 (Medline Abstract No. 94348160).

Desrouleaux et al. "Fatigue in Multiple Sclerosis: Pilot Trial of Selegiline", Neurology 41, 321 (Mar. 1991).

Physicians Desk Reference, 48$^{th}$, ed, 1994, pp. 2309–2311.

L. Steinman, Autoimmune Disease, Scientific American 1993 Sep. 269 (3):106–114.

*Primary Examiner*—Jeffrey C. Mullis
*Attorney, Agent, or Firm*—Kenyon & Kenyon

[57] ABSTRACT

The invention relates to a method of treating multiple sclerosis comprising administering an effective amount of (R)-(–)-N,2-dimethyl-N-2-propynylphenethylamine alone or in conjunction with an effective amount of interferon beta or an effective amount of amantadine.

6 Claims, No Drawings

METHOD FOR TREATING MULTIPLE SCLEROSIS

FIELD OF THE INVENTION

This invention relates to a method for treating multiple sclerosis and, more particularly, the use of (R)-(−)-N,2-dimethyl-N-2-propynylphenethylamine, commonly known as deprenyl, a monoamine oxidase inhibitor drug (MAO-inhibitor).

BACKGROUND OF THE INVENTION

Multiple sclerosis (MS) is a crippling disease that affects over 250,000 Americans. MS is characterized by neuron deterioration in the central nervous system with the associated lose of the insulating myelin sheath from around the axons of the nerve cells. This loss of myelin results in loss of electrical insulation and the "short-circuiting" of the electrical pathways mediated by the affected nerves and progressive neurological impairment. MS usually affects young adults in what should be the healthiest, most productive years of their lives and affects women more often than men.

The symptoms of MS include pain and tingling in the arms and legs; localized and generalized numbness, muscle spasm and weakness; bowel and bladder dysfunction; difficulty with balance when walking or standing; and fatigue. In most cases, people afflicted with MS lose the ability to stand and/or walk entirely. Optic neuritis may occur episodically throughout the course of the disease. The symptoms are exacerbated by physical fatigue or emotional stress.

Approximately half the people with this disease have relapsing-remitting MS in which there are unpredictable attacks where the clinical symptoms become worse (exacerbation) which are separated by periods of remission where the symptoms stabilize or diminish. The other half have chronic progressive MS without periods of remission.

Although the cause of MS remains unknown, medical research over the last fifteen years indicates that it is caused by an immune assault on the central nervous system. It has been hypothesized that in genetically susceptible people, an infection with adenovirus type-two sets off an ultimately self destructive chain of events within the immune system. See Scientific American. 1993; Vol. 269 (3), pages 106–114. It is known that many infectious organisms, in an attempt to evade the immune system, have developed surface mimicry to certain proteins that are normally found within the human body. In MS, the adenovirus type-two has a section of proteins on its surface which exactly matches the protein sequence on part of myelin basic protein found in the central nervous system. When the body makes T lymphocytes to attack this protein section on the surface of the adenovirus type-two organism to rid the body of the invading virus, these same T lymphocytes also attack the myelin basic protein in the brain and spinal cord. Because myelin acts as an insulating material along the electrically charged axons of nerves in the central nervous system, T lymphocyte mediated damage to axon myelin results in short-circuiting of these nerves with associated nerve dysfunction.

More recent research has indicated that this myelin attack has effects beyond the nerve axons. Along with the nerves that conduct electrical signals in the brain and spinal cord, there are repair cells called oligodendroglial cells. These cells are able to repair damaged myelin, and toward this end, the oligodendroglial cells contain myelin basic protein. While T lymphocytes are busy deranging the myelin insulating the nerve axons, B lymphocytes attack the myelin containing oligodendroglial cells with oxidase enzymes.

Thus, in multiple sclerosis not only is the nerve insulating myelin damaged, but the oligodendroglial cells which might repair this myelin damage are also attacked and their ability to repair damaged myelin is seriously compromised. See Scientific American. 1993; Vol. 269 (3), pages 106–114. This combined destructive effect could explain why multiple sclerosis is such a devastating disease. Researchers into Parkinson's disease have been able to detect large amounts of monoamine oxidase B which is stored within the oligodendroglial cells that normally support central nervous system neurons. Based on this work, it appears that lysed oligodendroglial cells release oxidizing enzymes and thus potentiate an attack on substantia nigra neurons.

When flare-ups and exacerbations in MS occur, patients are often treated with high doses of oral or intravenous steroids which may temporarily ameliorate some of the multiple sclerosis symptoms. But the gradual nervous system deterioration persists despite this treatment. Other attempts to treat the disease have involved therapies such as cyclosporine and cytoxan which suppress the immune system. However, these therapies have limited efficacy and significant toxicity.

Recently, the Food and Drug Administration approved interferon beta-1b ("Betaseron") as a treatment for multiple sclerosis. But even this expensive treatment promises only to reduce the frequency and severity of exacerbations, extending the time between relapses. It does not prevent exacerbations from occurring nor does it affect the patient's level of disability. The effect of interferon beta alone on the ultimate progression of multiple sclerosis over time is unknown.

Although universally effective immunotherapy for multiple sclerosis appears to be many years away, an anti-oxidative treatment would be desirable to prevent an oxidizing attack on oligodendroglial cells and thus reinstate the myelin repair capabilities of these support cells in the central nervous system. Such a reactivation of oligodendroglial cells would allow repair of T lymphocyte mediated myelin damage and restoration of normal nervous function.

At the present time, there is no widely applied safe and effective treatment for relapsing-remitting multiple sclerosis. It would be desirable then to find a drug regimen which is able to successfully treat multiple sclerosis. This treatment would represent a major benefit for people with multiple sclerosis. presently exists.

ADVANTAGES AND SUMMARY OF THE INVENTION

A principal objective of the present invention is to provide a novel and effective treatment for relapsing-remitting multiple sclerosis.

Another objective of the present invention is to provide a method for treating multiple sclerosis which is longer lasting and more cost effective than known treatment modalities.

The present invention provides a method for treating multiple sclerosis which comprises administering an effective amount of deprenyl.

The present invention further provides a method for attenuating lymphocytic attack on the central nervous system which comprises administering an effect amount of deprenyl.

The present invention also provides a method for treating multiple sclerosis which comprises administering an effective amount of deprenyl in combination with an effective amount of interferon beta.

The present invention also provides a method for attenuating the attack of B lymphocytes and T lymphocytes on the central nervous system comprising the administration of an effective mount of deprenyl and interferon beta.

Another object of the present invention is to provide s method for treating multiple sclerosis comprising the administration of an effective amount of deprenyl and an effective amount of amantadine.

Further objects of the present invention will be apparent and pointed out specifically in connection with the detailed description of the invention which follows:

DETAILED DESCRIPTION

The following examples of treatment of patients with relapsing/remitting multiple sclerosis further illustrate the present invention but are not construed to limit the scope thereof. Deprenyl was administered to a small group of patients with relapsing-remitting multiple sclerosis; all of the patients are still receiving the drug. Although these patients received deprenyl in daily dosages of 10–15 mg orally, deprenyl or its derivatives or analogues can be used in the manufacture of a medicament administered at 0.05–20.00 mg/day in single or divided doses by oral, parenteral or transdermal routes.

Test 1

Patient #1 was diagnosed by magnetic resonance imaging (MRI) as having Multiple Sclerosis at age 29. The patient's initial MS symptoms included numbness and tingling in the left hand migrating proximally into the left elbow. Motor weakness in right hand grasp and finger movement also waxed and waned. There was some slight left upper arm and left leg weakness as well, and the patient reported tingling in the left upper lip and along the left side of the neck. The patient also had slurred speech and difficulty masticating food.

Initially the patient was treated with high doses of intravenous steroids (ACTH), which resulted in fairly good resolution of the initial symptoms. Nine months later, the patient had a relapse manifested by numbness and tingling in the left arm and left leg, poor left eye accommodation, a painful pulling sensation in the left chest on sneezing, and difficulty maintaining balance while walking on forest trails at night. The patient was again treated with high dose intravenous ACTH, but some left hand numbness, slight dizziness, and poor left eye accommodation persisted.

One year after the initial diagnosis of MS, the patient was started on deprenyl, 5 mg two times daily. During the first month of deprenyl administration, there was some initial improvement in the dizziness and left hand numbness. The patient then ran out of deprenyl, and while off the deprenyl, the left hand numbness and dizziness recurred, along with difficulty maintaining balance while walking on forest trails at night. After resuming taking deprenyl, the patient was able to walk along forest trails at night for the first time in many months. Because there was some slight persisting dizziness and left hand numbness, the deprenyl dose was increased to 5 mg three times daily. After four weeks, the numbness gradually diminished, although the patient noticed some tinnitus and occasional head spinning sensation. Overall, the patient had an increased sense of well-being. On examination, the patient was found to have markedly improved accommodation in the left eye, and very slight tingling of the finger tips only.

After being on the higher dose of deprenyl for eight weeks, the patient ran out of deprenyl and took no deprenyl for eight weeks. The patient again had a flare-up manifested by numbness, weakness, and tingling in the right hand and arm, and left leg weakness causing the patient to drag the left foot. The patient was restarred on deprenyl 5 mg three times daily, and again given high dose ACTH treatment. Immediately following the high dose steroid treatment, right arm strength was improved, and right arm numbness and tingling was over a smaller area. After taking deprenyl consistently for the next 20 weeks, the patient had only slight tingling sensation in the left hand. In all other respects, sensation and motor function in all extremities had returned to normal.

Test 2

In patient #2, Multiple Sclerosis was diagnosed at age 35 by MRI scan. On examination prior to starting a regimen of deprenyl, the patient was found to have slight flexor and extensor weakness in the left leg, as well as slight, diffusely diminished sensation over the entire left leg. The patient had easy fatiguability, difficulty maintaining balance, and complained of pain across the mid-back and right side. These symptoms had been slowly worsening in recent months.

Initially the patient was treated with deprenyl 5 mg each morning once per day because of the patient's belief that the evening deprenyl dose was causing insomnia. After taking deprenyl once per day for eight weeks, the patient had only moderate weakness in the left quadriceps femoris muscle, and the MS symptoms stabilized. After sixteen weeks, the patient received deprenyl twice daily. One week later, the patient's left leg strength was generally improved, with only some moderate decreased tone and size of the left quadriceps femoris muscle. After sixteen weeks of therapy with deprenyl 5 mg twice daily, the patient was feeling well and was able to work five hour shifts as a supermarket checker. The patient was using a cane to help with walking. The patient had no numbness in the left leg, and the right and left quadriceps femoris muscles were of equal size, although the tone of the left quadriceps femoris muscle was not quite as good as the right. After 26 weeks of therapy, both the muscle size and tone of both quadriceps femoris muscles were equal and normal.

Five months later, after 46 weeks of therapy, the deprenyl dose was increased to 5 mg three times daily because the patient had persistent fatiguability and difficulty walking. After taking this higher dose of deprenyl for one week, the patient no longer required a cane for walking. After taking the higher deprenyl dose for eight weeks, the patient was found to have a right optic neuritis, which had been a problem earlier in the course of the patient's MS. However, this optic neuritis resolved over the next month without special treatment.

After six months of an deprenyl regimen of 5 mg three times daily, the patient was started on a concomitant regimen of Betaseton injections every other day. After some muscle cramping associated with the first dose, the patient then steadily improved, and the patient's overall energy level improved dramatically. After 8 weeks of the combination therapy of deprenyl, 5 mg, three time per day and every other day injections of Betaseron, the patient was feeling near-euphoric, and the left-dominant arm, hand, and leg, which had exhibited a greater amount of weakness, was actually getting stronger than the right side. Sensation was entirely normal and equal in all extremities.

Test 3

Patient #3 was first diagnosed with Multiple Sclerosis at age 28. When deprenyl was first administered to the patient at age 34, the patient's physical findings included loss of bladder control once daily, weakness in the right quadriceps femoris muscle, a painful right leg, impaired short term memory, impaired concentration, a right foot drop, halting speech, weakened right hand grasp, and weakness in the neck muscles that caused head droop. Medications taken at the time deprenyl 5 mg twice daily was started included amantadine 100 mg three times daily, desipramine 50 mg at bed time, and Ibuprofen 400 mg four times daily.

After being on deprenyl 5 mg twice daily for two weeks, the patient's right hand grasp was normal, mood was more positive, and the patient's speech was much less halting. The right foot drop persisted. After six weeks, the patient's speech was almost normal, and there was some slight improvement in the right foot dorsiflexion strength. And after eight weeks, the patient's urinary incontinence was no longer occurring daily, the patient was able to hold her head up for a longer period of time, and the right foot drop was only occurring intermittently. The patient was able to walk two blocks and experience only occasional dizziness. The patient had good grasp strength in both hands and good dorsiflexion strength in the right foot, although the left foot was still a bit stronger.

Following ten weeks on the twice per day dose of deprenyl, the patient's dose of amantadine was reduced to 100 mg twice daily. Four weeks later, the patient's right foot drop was gone, there was excellent muscle strength in the right quadriceps femoris muscle. Muscle strength in all four extremities was very good, but there was still a problem with slight dizziness on standing.

Eighteen weeks later, the patient depleted the supply of deprenyl and noticed an increase in over-all weakness, and became less mentally focused. On examination, the patient was found to have slight weakness in right foot dorsiflexion after being without deprenyl for one week. After deprenyl was resumed, the patient was able to begin working five to six hours per day after being completely disabled for some time. When unsteadiness became more of a problem in warm weather, the patient's dosage of amantadine was increased to 300 mg daily. Subsequently, there was strong right foot dorsiflexion, and the patient's speech was only slightly halting.

After 58 weeks, the patient's status was unchanged except for some bladder symptoms which were promptly resolved with antibiotic treatment. The patient was started on physical therapy to improve extremity strength.

After taking deprenyl for 94 weeks, the patient noticed increased problems with weakness of dorsiflexion in the right foot and more unsteadiness when walking. The deprenyl dose was increased to 5 mg three times daily, and the dosage of amantadine, which had been decreased to 200 mg per day, was increased to 300 mg daily. Within two weeks, the patient's right leg became much stronger, the dizziness and weakness on standing went away, and the patient was able to walk farther before becoming tired. The patient still had some numbness in the lower right calf and fingertips, but speech was clear and not at all halting. The patient's spirits were good, and motivational energy was excellent.

Patients treated with deprenyl have demonstrated consistently improved ambulatory abilities, improved stamina, and a striking lack of periodic relapses in multiple sclerosis. deprenyl can have dramatic therapeutic effects on patients with multiple sclerosis. Furthermore, these beneficial effects appear to be maintained over a period of years. Although, as demonstrated in the experience of Patient #1, relapses can be expected if patients stop taking deprenyl, the fact that Patient #1 had no relapses while taking deprenyl also indicates that deprenyl is able to prevent significant deterioration in patients with multiple sclerosis as long as the medication is taken consistently.

All three patient records indicate that a dose of deprenyl 5 mg three times daily is significantly more effective than a dose of 5 mg twice daily. The higher dose does not seem to be associated with any significant side effects.

Patient #2 is an example of administration of a higher dose of deprenyl with every other day injections of Betaseron. The patient's rapid improvement on the combination supports the hypothesis that deprenyl attenuates the B lymphocyte attack on the oligodendroglial repair cells in the central nervous system. While deprenyl alone facilitates the oligodendroglial cells' repair of myelin damage brought on by attacking T lymphocytes, and thus at least allows patients with multiple sclerosis to be maintained at a certain functioning level, the combination of deprenyl with Betaseron would attenuate both the B and T lymphocyte attacks on the central nervous system. This combination effect would be expected to result in a synergistic improvement in the multiple sclerosis patient, because for once the immune system would be free of significant damaging attacks. In fact, this is what was observed in Patient #2. In just a short period of time, the patient's mental lassitude that had plagued the patient since MS first appeared, disappeared. The patient's motivational energy improved as well, and the patient was able to handle things that would have seemed insurmountable in the past.

This synergistic improvement with deprenyl and Betaseron is not described in the benefits attributed to Betaseron in patients with multiple sclerosis; Betaseron alone is only able to lengthen the time between relapses in only 30% of patients with relapsing/remitting multiple sclerosis.

Thus, it appears that the best use of deprenyl to treat multiple sclerosis will be in combination with medications like Betaseron that attenuate the T lymphocyte attack on myelin in the central nervous system. Until the immune system malfunction that leads to multiple sclerosis can be manipulated, such a combination holds out hope that multiple sclerosis can be controlled, and in many cases, actually kept in a non-progressive, quiescent state. It also appears that the initiation of such combination treatment would be most effective when started as early in the disease as possible. Although relapses in patients with multiple sclerosis seem to be associated with some permanent damage to the central nervous system, this damage can be partially reversed with medications like deprenyl which facilitate healing in the central nervous system in these patients with multiple sclerosis.

I claim:

1. A method for treating multiple sclerosis comprising orally administering 15 mg to 20 mg daily of a compound (R)-(–)-N,2-dimethyl-N-2-propynylphenethylamine.

2. The method as recited in claim 1 wherein the amount of compound administered is 5 mg, three times daily.

3. The method as recited in claim 1 wherein the amount of compound administered is 5 mg, four times daily.

4. The method as recited in claim 1 wherein the amount of compound administered is 10 mg, two times daily.

5. The method as recited in claim 1 wherein the amount of compound administered is 15 mg, one time daily.

6. The method as recited in claim 1 wherein the amount of compound administered is 20 mg, one time daily.

* * * * *